United States Patent [19]

Prosen

[11] 4,253,869

[45] Mar. 3, 1981

[54] SEMI-PRECIOUS ALLOY

[75] Inventor: Emil M. Prosen, Bala-Cynwyd, Pa.

[73] Assignee: Neoloy Products, Inc., Posen, Ill.

[21] Appl. No.: 135,882

[22] Filed: Mar. 31, 1980

[51] Int. Cl.³ .............................................. C22C 19/07
[52] U.S. Cl. ..................................... 75/134 C; 75/171
[58] Field of Search ............................. 75/134 C, 171

[56] References Cited

U.S. PATENT DOCUMENTS 2,636,818  4/1953  Low ........................................ 75/171

Primary Examiner—R. Dean

Attorney, Agent, or Firm—Jacobs & Jacobs

[57] ABSTRACT

The present invention provides a semi-precious alloy especially adapted for use as an implant in orthopedic work and for use in dental work wherein it is important to have a corrosion-resistant alloy which has a very high tolerance for acceptance by the human body. In the preferred form of the invention the semi-precious alloy consists of the following elements, in parts by weight: cobalt 52%, chromium 22%, tungsten 10%, ruthenium 10%, molybdenum 2%, manganese 0.5%, niobium 0.5%, boron 0.17%, iron 1%, and copper 1%.

4 Claims, No Drawings

SEMI-PRECIOUS ALLOY

The present invention relates to semi-precious alloys for use in orthopedic and dental applications.

BACKGROUND OF THE INVENTION

In the orthopedic and dental art it is presently well known that various semi-precious alloys are provided for use as implants in bone structure such as jaws, hips, knees, ankles and the like, usually for the purpose of supporting the same and facilitating knitting of fractured bone elements, as well as strengthening the fractured area. In dentistry such implants are frequently embedded in bone and gum tissue.

In all of such implants it is absolutely essential that the alloy be corrosion-resistant; and one of the principal alloys which has been used for this purpose has consisted of cobalt, chromium and tungsten.

SUMMARY OF THE INVENTION

The present invention provides a semi-precious alloy especially adapted for use as an implant in orthopedic work and for use in dental work wherein it is important to have a corrosion-resistant alloy which has a very high tolerance for acceptance by the human body. In the preferred form of the invention the semi-precious alloy consists of the following elements, in parts by weight:

| | |
|---|---|
| Cobalt | 52% |
| Chromium | 22% |
| Tungsten | 10% |
| Ruthenium | 10% |
| Molybdenum | 2% |
| Manganese | 0.5% |
| Niobium | 0.5% |
| Boron | 0.17% |
| Iron | 1% |
| Copper | 1% |

DESCRIPTION OF THE INVENTION

According to the present invention a semi-precious alloy is provided which is especially adapted for use as an implant in orthopedic and dental work wherein it is important that the bone structure and gum or other tissue accept such implant and tolerate the same. As before mentioned there already exist in the art corrosion-resistant alloys for use as implants in body structure for orthopedic application which chiefly consist of cobalt, chromium and tungsten.

According to the present invention I have found that the addition of ruthenium (a precious metal) in the suggested part by weight of 10%, as shown in the above preferred formulation, substantially increases the corrosion resistance of the alloy and its tolerance in the human body. In fact, I have found on corrosion tests that the alloy of the present invention has higher corrosion resistance than any implant alloy available today. I have also found that the alloy has superior qualities to other precious metal implant alloys from the standpoint of physical properties.

As before mentioned, the preferred alloy of the present invention consists of the following elements, in parts by weight:

| | |
|---|---|
| Cobalt | 52% |
| Chromium | 22% |
| Tungsten | 10% |
| Ruthenium | 10% |
| Molybdenum | 2% |
| Manganese | 0.5% |
| Niobium | 0.5% |
| Boron | 0.17% |
| Iron | 1% |
| Copper | 1% |

It will be noted that in such preferred alloy ruthenium is provided in 10 parts by weight and that boron is also provided in a minor amount of 0.17 parts by weight.

This preferred alloy has a melting temperature of approximately 2700° F. and a Brinell hardness of 345.

The use of ruthenium as a precious metal makes the alloy an economical alloy for the reason that at the present time it is available at approximaately $30 per ounce, whereas, platinum sells for $1000 per ounce and gold at approximately $600 per ounce. Furthermore, ruthenium, which is produced as a by-product in the refining of platinum, has little commercial use at the present time. Thus, the alloy of the present invention, in addition to all of the other attributes set forth, has a practical advantage from the standpoint of the cost of its essential ingredients.

I have also found that the alloy of the present invention when cast to provide an orthopedic or dental appliance, when polished, gives a very high reflecting surface, almost resembling a diamond. This indicates to me, from my long experience with orthopedic and dental alloys, that such alloy is almost completely free of corrosive and other contaminant elements which are objectionable in orthopedic and dental work.

In its broadest form the invention may consist of the following elements in parts by weight:

| | |
|---|---|
| Cobalt | 48–58% |
| Chromium | 17–27% |
| Tungsten | 7–15% |
| Ruthenium | 7–15% |
| Molybdenum | 1–4% |
| Manganese | 0.5–1.5% |
| Niobium | 0.5–1.5% |
| Boron | 0.1–0.2% |
| Iron | 0.5–1.5% |
| Copper | 0.5–2% |

The alloy of the present invention is also adapted for use in dental restorations and particularly those dental restorations to which low-fusing porcelains are applied to their exterior surfaces. For porcelain application the coefficient of linear expansion of the alloy must be adjusted to closely match the coefficients of linear expansion of such porcelains. This is accomplished with the present invention by varying the parts by weight of cobalt, chromium, tungsten and ruthenium.

As is well understood in the art, in order to adhere low-fusing porcelain to a dental alloy, it is essential to provide on the surface of such alloy an oxide which promotes the adhesion of the porcelain with such alloy. With the present invention the elements niobium, copper, molybdenum, manganese and iron contribute to provide such an oxide on the surface of the alloy to promote the adhesion of the porcelain. In addition, I have found that ruthenium, which is a very corrosion-resistant element, on heating up to 1400° F., will oxidize and together with the other oxidizing elements form a very strong oxide on the surface of the alloy for the adhesion of low-fusing porcelains.

I am aware of dental alloys for application of porcelain wherein silicon is used as the fluxing agent for other elements. In the present application I prefer to replace silicon with boron in the small amount set forth. I have found that boron purifies the alloy and also acts as an adherent element for porcelain in the composition.

In general, the dental profession has been indoctrinated to use precious metals whenever possible, and platinum and gold have been high on the list of precious metals used by dentists. With the considerably higher prices of these two elements on the world market today, the cost of dental restorations using such elements has almost become prohibitive. Hence, the alloy of the present invention provides a practical solution to the problem of escalating dental appliance costs.

What I claim is:

1. A semi-precious alloy for use in orthopedic and dental appliances consisting essentially, in parts by weight, of:

| | |
|---|---|
| Cobalt | 48–58% |
| Chromium | 17–27% |
| Tungsten | 7–15% |
| Ruthenium | 7–15% |
| Molybdenum | 1–4% |
| Manganese | 0.5–1.5% |
| Niobium | 0.5–1.5% |
| Boron | 0.1–0.2% |
| Iron | 0.5–1.5% |
| Copper | 0.5–2% |

2. A semi-precious alloy for use in orthopedic and dental appliances consisting essentially, in parts by weight, of:

| | |
|---|---|
| Cobalt | 52% |
| Chromium | 22% |
| Tungsten | 10% |
| Ruthenium | 10% |
| Molybdenum | 2% |
| Manganese | 0.5% |
| Niobium | 0.5% |
| Boron | 0.17% |
| Iron | 1% |
| Copper | 1% |

3. A semi-precious alloy according to claim 1, wherein the melting temperature is approximately 2700° F. and the Brinell hardness is approximately 345.

4. A semi-precious alloy according to claim 1 which is especially adapted for the application of low-fusing porcelain thereto, wherein the proportions of cobalt, chromium, tungsten and ruthenium are varied within the limits set forth to provide an alloy having a coefficient of linear expansion closely approximating the coefficient of linear expansion of the low-fusing porcelain.

* * * * *